United States Patent [19]

Araki et al.

[11] Patent Number: 4,783,403

[45] Date of Patent: Nov. 8, 1988

[54] PROCESS FOR PRODUCING L-PHENYLALANINE

[75] Inventors: Kazumi Araki, Machida; Toshitsugu Ozeki; Yukiyoshi Ito, both of Yokkaichi; Shuichi Ishino, Machida; Hideharu Anazawa, Tokyo; Shigeru Kamimori, Matsusaka, all of Japan

[73] Assignee: Kyowa Hakko Kogyo Co., Ltd., Tokyo, Japan

[21] Appl. No.: 697,470

[22] Filed: Feb. 1, 1985

[30] Foreign Application Priority Data

Feb. 8, 1984 [JP] Japan .................................. 59-21400
Jun. 29, 1984 [JP] Japan .................................. 59-134535

[51] Int. Cl.$^4$ .................. C12P 13/22; C12N 9/10; C12R 1/01
[52] U.S. Cl. .................. 435/108; 435/193; 435/822; 435/830; 435/832; 435/843; 435/847; 435/850; 435/852; 435/859; 435/873; 435/877; 435/879; 435/881
[58] Field of Search .............. 435/108, 193, 822, 830, 435/832, 834, 840, 843, 847, 849, 850, 852, 859, 873, 877, 879, 881, 109

[56] References Cited

U.S. PATENT DOCUMENTS

| | | | |
|---|---|---|---|
| 3,198,712 | 8/1965 | Takahashi et al. | 435/109 |
| 3,759,790 | 9/1973 | Nakayama et al. | 435/108 |
| 3,767,528 | 10/1973 | Nagasaki et al. | 435/108 |
| 4,326,029 | 4/1982 | Yukawa et al. | 435/109 |
| 4,436,813 | 3/1984 | Wood et al. | 435/109 |
| 4,518,692 | 5/1985 | Rozzell | 435/116 |
| 4,525,454 | 6/1985 | Rozzell | 435/106 |
| 4,600,692 | 7/1986 | Wood et al. | 435/108 |

FOREIGN PATENT DOCUMENTS

| | | | |
|---|---|---|---|
| 0135846 | 4/1985 | European Pat. Off. | 435/106 |
| 0140503 | 5/1985 | European Pat. Off. | 435/106 |
| 2041418 | 2/1971 | Fed. Rep. of Germany | 435/108 |
| 2292041 | 6/1976 | France | 435/109 |

OTHER PUBLICATIONS

The Microbial Production of Amino Acids, 1972, pp. 441–446; Kodansha Scientific Books, Tokyo, JP, Chapter 16.2.1: "Production of Phenylalanine".
Chemical Abstracts, vol. 42, No. 21, Nov. 10, 1948, vol. 8874 f–g; Columbus Ohio, US M. G. Kritsman et al.: "Formation of Amino Nitrogen from Ammonia and Alpha-Keto Acids by Enzyme Preparations from Bacillus Subtilix & Biokhimiya 13, 327–31, 1948.
Chemical Abstracts, vol. 56, No. 8, Apr. 16, 1962, col. 9096i–9097a; Columbus, Ohio, US K. C. Saxena, et al.: "Transamination in Salmonella typhosa." J.DCI.IND. Research (India) 20 C, 287–91 (1961).
Patent Abstracts of Japan, vol. 10, No. 339 (C–385) (2395), Nov. 15, 1986 & JP-A-61 141 893 (Kyowa Hakko Kogyo Co. Ltd.) 28-06-1986.
Applied Microbiology, vol. 13, No. 4, Jul. 1965, pp. 618–624; Am. Soc. for Microbiology, US I. Chibata, et al.: "Amino Acid Isomerization in the Production of L-Phenylalanine from D-Phenylalanine by Bacteria."
Chemical Abstracts, vol. 74, No. 3, Jan. 18, 1971, p. 103 ref. no. 10662j; Columbus, Ohio, US Y. Tokoro, et al., "Microbial Production of L-Phenylalanine from N-Alkanes", & Agr. Biol. Chem. 1970, 34(10), 1516-21.
Chemical Abstracts, vol. 59, No. 5, Sep. 2, 1963, col. 5783 d–e; Columbus, Ohio US & JP-A-37 06 345 (Kyowa Fermentation Ind. Co., Ltd.) 28-06-1962.

Primary Examiner—Elizabeth Weimar
Attorney, Agent, or Firm—Antonelli, Terry & Wands

[57] ABSTRACT

L-phenylalanine is produced by using a microorganism belonging to the species *Citrobacter freundii, Erwinia herbicola, Enterobacter cloacae, Klebsiella oxytoca, Salmonella typhimurium, Bacillus cereus, Flavobacterium suaveolens, Serratia marcescens, Pseudomonas putida, Enterobacter cloacae, Proteus mirabilis, Paracoccus denitrificans, Arthrobacter globiformis, Bacillus sphaericus, Corynebacterium hydrocarboclastus, Kluyvera micum* or *Microbacterium ammoniaphilum* and having the ability to convert phenylpyruvic acid into L-phenylalanine in the presence of an amino group donor; or fumaric acid and ammonium ion or urea.

14 Claims, No Drawings

PROCESS FOR PRODUCING L-PHENYLALANINE

BACKGROUND OF THE INVENTION

The present invention relates to a process for producing L-phenylalanine. More particularly, the present invention relates to a process (process I) for producing L-phenylalanine which comprises culturing a microorganism belonging to the genus Citrobacter, Erwinia, Enterobacter, Klebsiella, Microbacterium, Salmonella, Bacillus, Corynebacterium or Flavobacterium having the ability to convert phenylpyruvic acid into L-phenylalanine in the presence of an amino group donor, in a culture medium containing phenylpyruvic acid and an amino group donor or alternatively, causing cells of the microorganism or product of treatment thereof to react on phenylpyruvic acid and an amino group donor in an aqueous solution: forming L-phenylalanine in the resultant culture broth or aqueous solution;and recovering L-phenylalanine therefrom.

Furthermore, the present invention relates to a process (process II) for producing L-phenylalanine which comprises culturing a microorganism belonging to the genus Serratia, Escherichia, Pseudomonas, Enterobacter, Salmonella, Erwinia, Proteus, Citrobacter, Paracoccus, Arthrobacter Bacillus, Brevibacterium, Corynebacterium. Flavobacterium, Klebsiella, Kluyvera or Micrococcus having the ability to convert phenylpyruvic acid into L-phenylalanine in the presence of fumaric acid and ammonium ion or urea, in a culture medium containing phenylpyruvic acid, fumaric acid and ammonium ion or urea or alternatively, causing cells of the microorganism or product of treatment thereof to react on phenylpyruvic acid, fumaric acid and ammonium ion or urea in an aqueous solution; forming L-phenylalanine in the resultant culture broth or aqueous solution and recovering L-phenylalanine therefrom.

L-phenylalanine is an amino acid which is useful as a raw material for a sweetening agent. It is an object of the present invention to provide an improved process for production of such amino acid on an industrial scale at low cost.

Heretofore, as the enzymatic processes for producing L-phenylalanine using phenylpyruvic acid as a susbstrate, the processes which cause cells of microorganisms belonging to the species *Agrobacterium tumefaciens* or *Proteus vulgaris* (Amino Acids, Vol. 2, page 18, 1960), the genus Alcaligenes, Pseudomonas, Aerobacter, Escherichia, Achromobacter, Sarcina, Kluyvera, or Micrococcus (Japanese Published Examined Patent Application No. 10672/62), the species *Serratia marcescens* (Amino Acids, Vol. 5, page 61, 1962), or the genus Aspergillus, Absidia, Cheatomium, Fusarium, Penicillium, Mucor, Monascus or Rhizopus (Japanese Published Examined Patent Application No. 20556/70) to react on phenylpyruvic acid and amino acids as amino group donors; and the processes which cause phenylpyruvic acid and amino group donors [such as nylon cylic oligomer (Japanese Published Examiner Patent Application No. 17991/69), nylon 6 hydrolyzate (Japanese Published Examined Patent Application No. 17992/69) and lactam (Japanese Published Examined Patent Application No. 17990/69)] to react on cells of a microorganism of the genus Corynebacterium have been known.

Although the processes exemplified above result in improved yields of L-phenylalanine, the production yields of such processes, nevertheless, are comparatively low from a commercial application standpoint. Thus, a need exists for a process for producing L-phenylalanine in higher yields at low cost.

To this end, it has now been found that L-phenylalanine is produced in higher yields by using the process of this invention; that is, process I or process II.

SUMMARY OF THE INVENTION

In accordance with the present invention, L-phenylalanine is produced by culturing a microorganism belonging to the genus Citrobacter, Erwinia, Enterobacter, Klebsiella, Microbacterium. Salmonella, Bacillus, Corynebacterium or Flavobacterium having the ability to convert phenylpyruvic acid into L-phenylalanine in the presence of an amino group donor, in a culture medium containing phenylpyruvic acid and an amino group donor or alternatively, causing cells of the microorganism or product of treatment thereof to react on phenylpyruvic acid and an amino group donor in an aqueous solution; forming L-phenylalanine in the resultant culture broth or aqueous solution and recovering L-phenylalanine therefrom; and also, is produced by culturing a microorganism belonging to the genus Serratia, Escherichia, Pseudomonas, Enterobacter, Salmonella, Erwinia, Proteus, Citrobacter, Paracoccus, Arthrobacter, Bacillus, Brevibacterium, Corynebacterium, Flavobacterium, Klebsiella, Kluyvera or Micrococcus having the ability to convert phenylpyruvic acid into L-phenylalanine in the presence of fumaric acid and ammonium ion or urea, in a culture medium containing phenylpyruvic acid, fumaric acid and ammonium ion or urea or alternatively, causing cells of the microorganism or product of treatment thereof to react on phenylpyruvic acid, fumaric acid and ammonium ion or urea in an aqueous solution: forming L-phenylalanine in the resultant culture broth or aqueous solution; and recovering L-phenylalanine therefrom.

DESCRIPTION OF THE INVENTION

The microorganism utilized in the present invention is a microorganism belonging to the genus Citrobacter, Erwinia, Enterobacter, Klebsiella, Microbacterium, Salmonella, Bacillus, Corynebacterium, Flavobacterium, Serratia, Escherichia, Pseudomonas, Proteus, Paracoccus, Arthrobacter, Brevibacterium, Kluyvera or Micrococcus which has the ability to convert phenylpyruvic acid into L-phenylalanine in the presence of an amino group donor or in the presence of fumaric acid and ammonium ion or urea. The microorganism may be a wild-type strain, a mutant strain or a recombinant strain derived by the technology of cell fusion, the technology of gene manipulation or other genetic procedures.

Examples of the preferred microorganism are *Citrobacter freundii* ATCC 6750, *Erwinia* herbicola ATCC 21434, *Enterobacter cloacae* ATCC 13047, *Klebsiella oxytoca* ATCC 8724, *Microbacterium ammoniaphilum* ATCC 15354, *Salmonella typhimurium* ATCC 19585, *Bacillus cereus* IFO 3131, *Corynebacterium glutamicum* ATCC 13032, *Flavobacterium suaveolens* ATCC 958, *Serratia marcescens* ATCC 13880, *Escherichia coli* ATCC 11303, *Pseudomonas putida* NRRL-B-11064, *Paracoccus denitrificans* ATCC 19367, *Proteus mirabilis* IFO 3849, *Arthrobacter globiformis* ATCC 8010, *Bacillus sphaericus* ATCC 10208, *Brevibacterium lactofermentum* ATCC 13655, *Corynebacterium hydrocarboclastus*

ATCC 15108, *Kluyvera cryocrescens* ATCC 14237 and *Micrococcus luteus* ATCC 10240.

These ATCC strains are deposited with the American Type Culture Collection, U.S.A. and are available to the public therefrom. The strain NRRL-B-11064 is deposited with ARS Culture Collection Research Fermentation Laboratory, U.S.A. and is also freely available. The strains IFO 3131 and IFO 3849 are deposited with Institute for Fermentation, saka, Japan, and is also freely available.

As the medium in which the microorganisms as described above are cultured to produce L-phenylalanine, either a natural medium or synthetic medium may be employed so long as it contains carbon sources, nitrogen sources, inorganic salts, etc.

As the carbon source, carbohydrates such as glucose, fructose, sucrose, maltose, mannose, starch, starch hydrolyzate, molasses and fruit juices, sugar alcohols such as glycerol, sorbitol and mannitol, organic acids such as acetic acid, formic acid, fumaric acid, malic acid, citric acid and gluconic acid, alcohols such as methanol, ethanol and propanol may be used.

As the nitrogen source, in the case of process I, ammonia or inorganic and organic ammonium salts such as ammonium chloride, ammonium sulfate, ammonium acetate and ammonium phosphate, nitrogen-containing compounds such as urea, amines, peptone, meat extract, yeast extract, corn steep liquor, caseine hydrolyzate, soybean cake hydrolyzate, various fermented cells and digested products thereof may be used; and in the case of process II ammonia or ammonium salts such as ammonium chloride, ammonium sulfate, ammonium carbonate, ammonium acetate and ammonium phosphate, nitrogen compounds such as urea, amino acids such as glutamic acid, aspartic acid, methionine, glycine, lysine, arginine and ornithine, and natural nutrients such as peptone, yeast extract, casein hydrolyzate, defatted soybean and its digested products may be used.

As the inorganic material, potassium dihydrogen phosphate, dipotassium hydrogen phosphate, magnesium phosphate, magnesium sulfate, sodium chloride, ferrous sulfate, manganese sulfate and calcium carbonate may be used.

When the microorganism to be used in the present invention requires specific nutrients for its growth, it is, of course, also necessary to add appropriate amounts of these substances to the medium. In some cases, such nutrients may be supplied by natural materials mentioned above as examples of the nitrogen source.

In case of process I, phenylpyruvic acid and the amino group donor is added to the aforementioned culture medium either from the beginning of culturing or during the course of the culturing.

As the amino group donor, L-glutamic acid, L-aspartic acid, L-leucine, L-lysine, D or L-methionine, glycine, L-lysine, L-ornithine and D or L-alanine may be used. They are used in the form of final products manufactured by the fermentation method or chemical synthesis method, crude products obtained during the course of such manufacture, amino acid fermentation broths produced. by the fermentation method and the enzyme method, and reaction solutions.

In case of process II, phenylpyruvic acid, fumaric acid and ammonium ion or urea are added to the culture medium either from the beginning of culturing or during the course of culturing.

Phenylpyruvic acid and fumaric acid are each used in the form of salts such as ammonium salt, sodium salt, potassium salt or calcium salt.

Ammonium ion is supplied in the form of a salt such as ammonium sulfate, ammonium phosphate, ammonium nitrate, ammonium chloride, ammonium acetate, ammonium formate, ammonium fumarate, or ammonium malate, or in the form of ammonia water or ammonia gas.

In case of processes I and II, culturing is carried out by aeration-agitation of a pH of from 3 to 10, preferably 6 to 9, and at a temperature of from 20° to 60° C., preferably 25° to 40° C. for 1 to 5 days.

As the result, L-phenylalanine is formed in the culture broth.

The enzymatic process for producing L-phenylalanine using cells of the microorganism mentioned above or product of treatment thereof is explained hereinafter.

As the composition of the culture medium and the culture conditions in case of obtaining the cells of the miroorganism, the same composition and condition as described above are used.

The microbial cells thus obtained are used without any further treatment for the reaction. Optionally the cells are subjected to various treatments and the products of such treatments may be used for the reaction.

As the microbial cells, cells themselves or culture broth containing cells may be used.

As the treated product of cells, the product of mechanical attrition of cells, the product of treatment with ultrasonic waves, the product of lyophilization, the product of treatment with solvent, the product of treatment with enzyme, the product of desiccation, the product of treatment with surfactant, the protein fraction of cells and the immobilization products of cells and products of cell treatment may be used.

In the case of process I', the reaction is effected by causing the cells obtained as described above or the product of their treatment to react upon phenylpyruvic acid and an amino group donor.

As the amino group donor, the same donor as mentioned above may be used.

For the purpose of the reaction, the concentration of phenylpyruvic acid is in the range of 0.01 to 1M, and that of amino group donor in the range of 0.01 to 2M.

These raw materials are supplied all at once or intermittently.

In case of process II, the reaction is effected by causing the cells obtained as described above or the product of their treatment to react upon (1) phenylpyruvic acid, (2) fumaric acid and (3) ammonium ion or urea in an aqueous solution.

The phenylpyruvic acid, fumaric acid and ammonium ion to be used for the reaction are the same as those used for the culture described above.

For the purpose of the reaction, the concentration of phenylpyruvic acid is in the range of 0.01 to 1M, that of fumaric acid in the range of 0.01 to 2M, and that of ammonium ion or urea in the range of 0.01 to 10M. These raw materials are supplied all at once or intermittently.

In the processes I and II, the reaction is carried out at a pH of from 4 to 10, preferably 6 to 9and at a temperature of from 10° to 70° C., preferably 25° to 45° C., for 1 to 48 hours.

As the result, L-phenylalanine is formed in the aqueous solution.

Recover of L-phenylalanine from the culture broth or the aqueous solution is effected by means of ion-exchange resin or active carbon adsorption.

Practice of specific embodiments of the invention is illustrated by the following representative examples.

EXAMPLE 1

One loop of each of the microorganisms shown in Table 1 was inoculated into a test tube containing 10 ml of a culture medium (pH 7.0) comprising 0.5% glucose, 0.3% yeast extract, 1% meat extract, 1% peptone and 0.3% sodium chloride.

Culturing was carried out at 28° C. for 18 hours, with shaking (210 rpm).

After completion of the culturing, the test tube was centrifuged to gather cells, washed twice by centrifugation with 10 ml each of an aqeuous 0.85% sodium chloride solution. Then, 1.5 ml of a reaction solution of the following composition was poured into the test tube and the reaction was carried out for 18 hours under the same conditions as described above. As the result, L-phenylalanine was formed in a concentration shown in The composition of the reaction solution is as follows: 50 mM sodium β-phenylpyruvic acid, 200 μM pyridoxal phosphate, 100 mM Tris buffer (pH 7.4), and 100 mM L-sodium glutamate or 100 mM L-sodium aspartate as an amino group donor.

TABLE 1

| Microorganism Used | Yield of L-phenylalanine (mg/ml) | |
| --- | --- | --- |
|  | L-sodium glutamate | L-sodium aspartate |
| Citrobacter freundii ATCC 6750 | 5.3 | 2.8 |
| Erwinia herbicola ATCC 21434 | 2.5 | 1.3 |
| Enterobacter cloacae ATCC 13047 | 4.8 | 3.1 |
| Klebsiella oxytoca ATCC 8724 | 4.7 | 2.8 |
| Microbacterium ammoniaphilum ATCC 15354 | 3.1 | 0.8 |
| Salmonella typhimurium ATCC 19585 | 5.1 | 2.7 |

EXAMPLE 2

The same procedure as described in Example 1 was repeated except that microorganisms shown in Table 2 was used. The results are shown in Table 2.

TABLE 2

| Microorganism Used | Yield of L-phenylalanine (mg/ml) | |
| --- | --- | --- |
|  | L-sodium glutamate | L-sodium aspartate |
| Bacillus cereus IFO 3131 | 2.0 | 1.7 |
| Corynebacterium glutamicum ATCC 13032 | 2.8 | 0.96 |
| Flavobacterium suaveolens ATCC 958 | 3.0 | 1.8 |

EXAMPLE 3

Citrobacter freundii ATCC 6750 was used as a seed strain. One loop of cells of the microorganism was inoculated into 5 ml of a fermentation medium of the following composition in a test tube.

Culturing was carried out at 28° C. for 5 hours with shaking (210 rpm). Then, 0.5 ml of an aqueous sodium phenylpyruvate solution in a concentration of mg/ml (passed through a membrane filter for removal of microbial cells) was added to the culture broth and culturing was continued for 24 hours in total. After completion of the culturing, 3.8 mg/ml L-phenylalanine was accumulated in the supernatant. As a control, when the same procedure was conducted in the absence of phenylpyruvic acid, not more than 0.1 mg/ml L-phenylalanine was accumulated in the supernatant. Composition of fermentation medium:

5% glucose, 0.5% ammonium sulfate, 0.8% sodium glutamate, 0.05% $KH_2PO_4$, 0.05% $K_2HPO_4$, 0.025% $MgSO_4.7H_2O$, 0.05% corn steep liquor and 2% $CaCO_3$ (pH 7.0, neutralized with ammonia water).

EXAMPLE 4

One loop of each of microorganisms shown in Table 3 was inoculated into 10 ml of a culture medium (pH 7.0) comprising 0.5% glucose, 0.3% yeast extract and 1.5% powdery meat extract in a test tube. Culturing was carried out at 28° C. for 18 hours with shaking (210 rpm).

After completion of the culturing, the cells were centrifuged and put to frozen storage (−20° C.). After one day's frozen storage, 10 ml of an aqueous 0.85% sodium chloride solution was added thereto. The cells were dissolved, and subjected to centrifugation and washing. The cells thus obtained were suspended in 1.5 ml of a reaction solution of the following composition and allowed to stand at 40° C. for 18 hours. L-phenylalanine was formed at concentrations shown in Table 3.

the composition of the reaction solution is as follows:
100 mM sodium β-phenylpyruvate, 200 νM pyridoxalphosphate, 200 mM Tris-buffer (pH 8.4) and 200 mM ammonium fumarate.

TABLE 3

| Microorganism Used | Yield of L-phenylalane (mg/ml) |
| --- | --- |
| Serratia marcescens ATCC 13880 | 4.7 |
| Escherichia coli ATCC 11303 | 13.5 |
| Pseudomonas putida NRRL-B-11064 | 14.6 |
| Enterobacter cloacae ATCC 13047 | 13.0 |
| Salmonella typhimurium ATCC 19585 | 11.7 |
| Erwinia herbicola ATCC 21434 | 1.2 |
| Proteus mirabilis IFO 3849 | 14.8 |
| Citrobacter freundii ATCC 6750 | 13.0 |
| Paracoccus denitrificans ATCC 19367 | 3.4 |
| Arthrobacter globiformis ATCC 8010 | 1.0 |
| Bacillus sphaericus ATCC 10208 | 0.7 |
| Brevibacterium lactofermentum ATCC 13655 | 0.4 |
| Corynebacterium hydrocarboclastus ATCC 15108 | 0.3 |
| Flavobacterium suaveolens ATCC 958 | 1.4 |
| Klebsiella oxytoca ATCC 8724 | 7.5 |
| Kluyvera cryorescens ATCC 14237 | 3.0 |
| Micrococcus luteus ATCC 10240 | 2.0 |

EXAMPLE 5

The same procedure as described in Example 4 was repeated with the cells of Proteus mirabilis IFO 3849 except that a reaction solution of the following composition was used. Consequently, 8.3 mg/ml L-phenylalanine was formed in the reaction solution. Composition of reaction solution:

100 mM sodium β-phenylpyruvic acid, 200 mM pyridoxal phosphate, 100 mM sodium fumarate, mM urea, 100 mM Tris buffer (pH 8.4).

What is claimed is:

1. A process for producing L-phenylalanine which comprises culturing a microorganism belonging to the species *Citrobacter freundii, Erwinia herbicola, Enterobacter cloacae, Klebsiella oxytoca, Salmonella typhimurium,* or *Flavobacterium suaveolens* and having the ability to convert phenylpyruvic acid into L-phenylalanine in the presence of an amino group donor, in a culture medium containing phenylpyruvic acid and an amino group donor, forming L-phenylalanine in the resultant culture broth and recovering L-phenylalanine therefrom.

2. The process according to claim 1, wherein the microorganism is *Citrobacter freundii* ATCC 6750, *Erwinia herbicola* ATCC 21434, *Enterobacter cloacae* ATCC 13047, *Klebsiella oxytoca* ATCC 8724, *Salmonella typhimurium* ATCC 19585, or *Flavobacterium suaveolens* ATCC 958.

3. The process according to claim 1, wherein the amino group donor is L-glutamic acid, L-aspartic acid. L-leucine, L-lysine, D or L-methionine, glycine, L-arginine, D or L-alanine or L-ornithine.

4. The process according to claim 1, wherein the culturing in the culture medium is carried out at a pH of from 3 to 10 at a temperature of 20° to 60° C. for 1 to 5 days.

5. A process for producing L-phenylalanine which comprises contacting a cell product of a microorganism belonging to the species *Citrobacter freundii, Erwinia herbicola, Enterobacter cloacae, Klebsiella oxytoca, Salmonella typhimurium,* or *Flavobacterium suaveolens* having the ability to convert phenylpyruvic acid into L-phenylalanine inthe presence of an amino group donor, with phenylpyruvic acid and an amino group donor in an aqueous solution, forming L-phenylalanine in the aqueous solution and recovering L-phenylalanine therefrom.

6. The process according to claim 5, wherein the reaction is carried out in the aqueous solution at a pH of from 4 to 10 at a temperature of 10° to 70° C. for 1 to 48 hours.

7. The process according to claim 5, wherein the microorganism is *Citrobacter freundii* ATCC 6750, *Erwinia herbicola* ATCC 21434, *Enterobacter cloacae* ATCC 13047, *Klebsiella oxytoca* ATCC 8724, *Salmonella typhimurium* ATCC 19585, or *Flavobacterium suaveolens* ATCC 958.

8. The process according to claim 5, wherein the amino group donor is L-glutamic acid, L-aspartic acid, L-leucine, L-lysine, D- or L-methionine, glycine, L-arginine, D- or L-alanine or L-orinithine.

9. A process for producing L-phenylalanine which comprises culturing a microorganism belonging to the species *Serratia marcescens, Pseudomonas putida , Enterobacter cloacae, Salmonella typhimurium, Erwinia herbicola, Proteus mirabilis, Citrobacter freundii, Paracoccus denitrificans, Arthrobacter globiformis, Bacillus sphaericus, Corynebacterium hydrocarboclastus, Flavobacterium suaveolens, Klebsiella oxytoca, Kluyvera cryocrescens* or *Micrococcus luteus* and having the ability to convert phenylpyruvic acid into L-phenylalanine in the presence of fumaric acid and ammonium ion or urea in a culture medium containing phenylpyruvic acid, fumaric acid and ammonium ion or urea, forming L-phenylalanine in the resultant culture broth and recovering L-phenylalanine therefrom.

10. The process according to claim 7, wherein the microorganimm is *Serratia marcescens* ATCC 13880, *Escherichia coli* ATCC 11303, *Pseudomonas putida* NRRL-B-11064, *Enterobacter cloacae* ATCC 13047, *Salmonella typhimurium* ATCC 19585, *Erwinia herbicola* ATCC 21434, *Proteus mirabilis* IFO 3849, *Citrobacter freundii* ATCC 6750, *Paracoccus denitrificans* ATCC 19367, *Arthrobacter globiformis* ATCC 8010, *Bacillus sphaericus* ATCC 10208, *Brevibacterium lactofermentum* ATCC 13655, *Corynebacterium hydrocarboclastus* ATCC 15108, *Flavobacterium suaveolens* ATCC 958, *Klebsiella oxytoca* ATCC 8724, *Kluyvera cryocrescens* ATCC 14237 or *Micrococcus luteus* ATCC 10240.

11. The process according to claim 9, wherein the culturing in the culture medium is carried out at a pH of from 3 to 10 at a temperature of 20° to 60° C. for 1 to 5 days.

12. A process for producing L-phenylalanine which comprises contacting a cell product of a microorganism belonging to the species *Serratia marcescens, Pseudomonas putida, Enterobacter cloacae, Salmonella typhimurium, Erwinia herbicola, Proteus mirabilis, Citrobacter freundii, Paracoccus denitrificans, Arthrobacter globiformis, Bacillus sphaericus, Corynebaterium hydrocarboclastus, Flavobacterium suaveolens, Klebsiella oxytoca, Kluyvera cryocrescens* or *Micrococcus luteus* and having the ability to convert phenylpyruvic acid into L-phenylalanine in the presence of fumaric acid and ammonium ion or urea, with phenylpyruvic acid, fumaric acid and ammonium ion or urea in an aqueous solution, forming L-phenylalanine in the aqueous solution and recovering L-phenylalanine therefrom.

13. The process according to claim 12, wherein the reaction is carried out in the aqueous solution at a pH of from 4 to 10 at a temperature of 10° to 70° C. for 1 to 48 hours.

14. The process according to claim 12, wherein the microorganism is *Serratia marcescens* ATCC 13880, *Pseudomonas putida* NRRL-B-11064, *Enterobacter cloacae* ATCC 13047, *Salmonella typhimurium* ATCC 19585, *Erwinia herbicola* ATCC 21434, *Proteus mirabilis* IFO 3849, *Citrobacter freundii* ATCC 6750, *Paracoccus denitrificans* ATCC 19367, *Arthrobacter globiformis* ATCC 8010, *Bacillus sphaericus* ATCC 10208, *Corynebacterium hydrocarboclastus* ATCC 15108, *Flavobacterium suaveolens* ATCC 958, *Klebsiella oxytoca* ATCC 8724, *Kluyvera cryocrescens* ATCC 14237 or *Micrococcus luteus* ATCC 10240.

* * * * *